(12) United States Patent
Ekman et al.

(10) Patent No.: US 11,813,436 B2
(45) Date of Patent: Nov. 14, 2023

(54) AUTO-INJECTOR

(71) Applicant: Sanofi-Aventis Deutschland GMBH, Frankfurt am Main (DE)

(72) Inventors: Matthew Ekman, Cheshire (GB); Yannick Hourmand, Haslingfield (GB); Timothy Donald Barrow-Williams, St. Albans Herts (GB)

(73) Assignee: Sanofi-Aventis Deutschland GMBH, Frankfurt am Main (DE)

( * ) Notice: Subject to any disclaimer, the term of this patent is extended or adjusted under 35 U.S.C. 154(b) by 0 days.

(21) Appl. No.: 18/144,555

(22) Filed: May 8, 2023

(65) Prior Publication Data
US 2023/0270944 A1    Aug. 31, 2023

Related U.S. Application Data

(63) Continuation of application No. 17/719,441, filed on Apr. 13, 2022, which is a continuation of application
(Continued)

(30) Foreign Application Priority Data

Jun. 28, 2010   (EP) .................................. 10167506

(51) Int. Cl.
*A61M 5/20* (2006.01)
*A61M 5/32* (2006.01)

(52) U.S. Cl.
CPC ........ *A61M 5/2033* (2013.01); *A61M 5/3202* (2013.01); *A61M 5/3257* (2013.01); *A61M 2005/206* (2013.01); *A61M 2005/208* (2013.01)

(58) Field of Classification Search
CPC .......... A61M 5/2033; A61M 2005/206; A61M 2005/208; A61M 5/3257; A61M 5/3202
See application file for complete search history.

(56) References Cited

U.S. PATENT DOCUMENTS 5,042,977 A * 8/1991 Bechtold ................. A61M 5/20
                                                              604/218
5,137,516 A    8/1992 Rand
(Continued)

FOREIGN PATENT DOCUMENTS

CH        705992       6/2013
CN       1901957       1/2007
(Continued)

OTHER PUBLICATIONS

International Preliminary Report on Patentability in Application No. PCT/EP2012/052647, dated Aug. 21, 2013, 8 pages.
(Continued)

*Primary Examiner* — Jason E Flick
(74) *Attorney, Agent, or Firm* — Fish & Richardson P.C.

(57) ABSTRACT

Auto-injector for administering a dose of a liquid medicament includes a housing to contain a syringe with a hollow needle and a stopper for sealing the syringe and displacing the medicament, the housing having a distal end and a proximal end with an orifice to apply against an injection site. A spring means, upon activation, can push the needle from inside the housing through the orifice and past the proximal end, operate the syringe to supply the dose of medicament, and retract the syringe with the needle after delivering the medicament. An activating means can lock the spring means in a pressurized state prior to manual operation and capable of, upon manual operation, releasing the spring means for injection.

30 Claims, 3 Drawing Sheets

Related U.S. Application Data

No. 16/809,669, filed on Mar. 5, 2020, now Pat. No. 11,311,671, which is a continuation of application No. 15/880,251, filed on Jan. 25, 2018, now Pat. No. 10,603,436, which is a continuation of application No. 15/165,720, filed on May 26, 2016, now Pat. No. 9,931,471, which is a continuation of application No. 13/806,324, filed as application No. PCT/EP2011/060726 on Jun. 27, 2011, now Pat. No. 9,352,088.

(56) References Cited

U.S. PATENT DOCUMENTS

| | | |
|---|---|---|
| 5,267,963 A | 12/1993 | Bachynsky |
| 5,320,609 A | 6/1994 | Haber |
| 5,681,291 A | 10/1997 | Galli |
| 5,746,215 A | 5/1998 | Brunnherg et al. |
| 6,004,297 A | 12/1999 | Steenfeldt-Jensen et al. |
| 6,159,181 A | 12/2000 | Crossman et al. |
| 6,221,046 B1 | 4/2001 | Burroughs |
| 6,270,479 B1 | 8/2001 | Manjarrez |
| 6,277,099 B1 | 8/2001 | Strowe et al. |
| 6,454,743 B1 | 9/2002 | Weber |
| 6,620,137 B2 | 9/2003 | Kirchhofer et al. |
| 7,195,616 B2 | 3/2007 | Diller et al. |
| 7,291,132 B2 | 11/2007 | DeRuntz et al. |
| 7,297,135 B2 | 11/2007 | Jeffrey |
| 7,341,575 B2 | 3/2008 | Rice et al. |
| 7,361,160 B2 | 4/2008 | Hommann |
| 7,407,494 B2 | 8/2008 | Bostrom et al. |
| 7,442,185 B2 | 10/2008 | Amark et al. |
| 7,597,685 B2 | 10/2009 | Olson |
| 7,678,085 B2 | 3/2010 | Graf |
| 7,717,877 B2 | 5/2010 | Lavi et al. |
| 7,749,195 B2 | 7/2010 | Hommann |
| 7,758,550 B2 | 7/2010 | Bollenbach et al. |
| 7,771,398 B2 | 8/2010 | Knowles et al. |
| 7,976,494 B2 | 7/2011 | Kohlbrenner et al. |
| 8,038,649 B2 | 10/2011 | Kronestedt |
| 8,048,037 B2 | 11/2011 | Kohlbrenner et al. |
| 8,062,255 B2 | 11/2011 | Brunnberg et al. |
| 8,083,711 B2 | 12/2011 | Enggaard |
| 8,308,695 B2 | 11/2012 | Laiosa |
| 8,323,238 B2 | 12/2012 | Cronenberg et al. |
| 8,357,125 B2 | 1/2013 | Grunhut et al. |
| 8,361,025 B2 | 1/2013 | Lawlis et al. |
| 8,366,680 B2 | 2/2013 | Raab |
| 8,376,993 B2 | 2/2013 | Cox et al. |
| 8,376,997 B2 | 2/2013 | Hogdahl et al. |
| 8,403,883 B2 | 3/2013 | Fayyaz et al. |
| 8,409,141 B2 | 4/2013 | Johansen et al. |
| 8,409,148 B2 | 4/2013 | Fiechter et al. |
| 8,439,864 B2 | 5/2013 | Galbraith et al. |
| 8,491,538 B2 | 7/2013 | Kohlbrenner et al. |
| 8,568,359 B2 | 10/2013 | Carrel et al. |
| 8,617,109 B2 | 12/2013 | Kronestedt et al. |
| 8,617,124 B2 | 12/2013 | Wieselblad et al. |
| 8,632,507 B2 | 1/2014 | Bartha |
| 8,684,969 B2 | 4/2014 | Moller et al. |
| 8,708,973 B2 | 4/2014 | Holmqvist |
| 8,734,402 B2 | 5/2014 | Sharp et al. |
| 8,758,292 B2 | 6/2014 | Tschirren et al. |
| 8,808,250 B2 | 8/2014 | Ekman et al. |
| 8,808,251 B2 | 8/2014 | Raab et al. |
| 8,821,451 B2 | 9/2014 | Daniel |
| 8,834,431 B2 | 9/2014 | Kohlbrenner et al. |
| 8,840,591 B2 | 9/2014 | Raab et al. |
| 8,882,723 B2 | 11/2014 | Smith et al. |
| 8,911,411 B2 | 12/2014 | Nielsen |
| 8,939,934 B2 | 1/2015 | Brereton et al. |
| 8,945,063 B2 | 2/2015 | Wotton et al. |
| 8,956,331 B2 | 2/2015 | Johansen et al. |
| 8,961,473 B2 | 2/2015 | Heald |
| 8,968,256 B2 | 3/2015 | Raab |
| 8,968,258 B2 | 3/2015 | Nzike et al. |
| 8,992,484 B2 | 3/2015 | Radmer et al. |
| 8,992,487 B2 | 3/2015 | Eich et al. |
| 9,005,160 B2 | 4/2015 | Karlsson et al. |
| 9,011,386 B2 | 4/2015 | Kronestedt et al. |
| 9,011,387 B2 | 4/2015 | Ekman et al. |
| 9,022,982 B2 | 5/2015 | Karlsson et al. |
| 9,022,991 B1 | 5/2015 | Moeller |
| 9,022,993 B2 | 5/2015 | Dasbach et al. |
| 9,022,994 B2 | 5/2015 | Moser et al. |
| 9,044,548 B2 | 6/2015 | Miller et al. |
| 9,044,553 B2 | 6/2015 | James et al. |
| 9,057,369 B2 | 6/2015 | Kohlbrenner et al. |
| 9,061,104 B2 | 6/2015 | Daniel |
| 9,067,024 B2 | 6/2015 | Roberts et al. |
| 9,072,838 B2 | 7/2015 | Hogdahl |
| 9,089,652 B2 | 7/2015 | Nzike et al. |
| 9,108,002 B2 | 8/2015 | Markussen |
| 9,125,988 B2 | 9/2015 | Karlsson |
| 9,132,235 B2 | 9/2015 | Holmqvist |
| 9,132,236 B2 | 9/2015 | Karlsson et al. |
| 9,155,844 B2 | 10/2015 | Brereton et al. |
| 9,199,038 B2 | 12/2015 | Daniel |
| 9,205,199 B2 | 12/2015 | Kemp et al. |
| 9,233,214 B2 | 1/2016 | Kemp et al. |
| 9,233,215 B2 | 1/2016 | Hourmand et al. |
| 9,242,044 B2 | 1/2016 | Markussen |
| 9,242,047 B2 | 1/2016 | Brereton et al. |
| 9,272,098 B2 | 3/2016 | Hourmand et al. |
| 9,283,326 B2 | 3/2016 | Kemp et al. |
| 9,283,327 B2 | 3/2016 | Hourmand et al. |
| 9,283,328 B2 | 3/2016 | Dasbach |
| 9,308,327 B2 | 4/2016 | Marshall et al. |
| 9,333,304 B2 | 5/2016 | Brereton et al. |
| 9,339,607 B2 | 5/2016 | Langley et al. |
| 9,352,088 B2 | 5/2016 | Ekman et al. |
| 9,352,090 B2 | 5/2016 | Brereton |
| 9,358,345 B2 | 6/2016 | Brereton et al. |
| 9,358,351 B2 | 6/2016 | Ekman et al. |
| 9,393,368 B2 | 7/2016 | Nzike et al. |
| 9,408,976 B2 | 8/2016 | Olson et al. |
| 9,408,977 B2 | 8/2016 | Butler et al. |
| 9,408,979 B2 | 8/2016 | Veasey et al. |
| 9,415,165 B2 | 8/2016 | Cowe |
| 9,421,336 B2 | 8/2016 | Ekman et al. |
| 9,427,525 B2 | 8/2016 | Barrow-Williams et al. |
| 9,427,527 B2 | 8/2016 | Dasbach et al. |
| 9,446,195 B2 | 9/2016 | Kramer et al. |
| 9,446,196 B2 | 9/2016 | Hourmand et al. |
| 9,446,201 B2 | 9/2016 | Holmqvist |
| 9,457,149 B2 | 10/2016 | Kemp et al. |
| 9,457,152 B2 | 10/2016 | Raab et al. |
| 9,492,622 B2 | 11/2016 | Brereton et al. |
| 9,707,343 B2 | 7/2017 | Fabien et al. |
| 9,717,851 B2 | 8/2017 | Fabien et al. |
| 9,895,492 B2 | 2/2018 | Fabien et al. |
| 9,931,471 B2 | 4/2018 | Ekman et al. |
| 10,420,898 B2 | 9/2019 | Daniel |
| 10,500,337 B2 | 12/2019 | Fabien et al. |
| 10,603,436 B2 | 3/2020 | Ekman et al. |
| 11,311,671 B2 | 4/2022 | Ekman et al. |
| 2001/0005781 A1 | 6/2001 | Bergens et al. |
| 2002/0007154 A1 | 1/2002 | Hansen et al. |
| 2002/0095120 A1 | 7/2002 | Larsen et al. |
| 2002/0123675 A1 | 9/2002 | Trautman et al. |
| 2003/0105430 A1 | 6/2003 | Lavi et al. |
| 2004/0039336 A1 | 2/2004 | Amark et al. |
| 2005/0027255 A1 | 2/2005 | Lavi et al. |
| 2005/0272551 A1 | 2/2005 | Lavi et al. |
| 2005/0101919 A1* | 5/2005 | Brunnberg ............ A61M 5/326 604/197 |
| 2005/0222539 A1 | 10/2005 | Gonzales et al. |
| 2006/0153693 A1 | 7/2006 | Fiechter et al. |
| 2006/0287630 A1 | 12/2006 | Hommann |
| 2007/0005021 A1 | 1/2007 | Kohlbrenner et al. |
| 2007/0027430 A1 | 2/2007 | Hommann |
| 2007/0112310 A1 | 5/2007 | Lavi et al. |
| 2007/0197975 A1 | 8/2007 | Burren et al. |
| 2008/0009807 A1 | 1/2008 | Hommann |
| 2008/0015520 A1 | 1/2008 | Hommann et al. |
| 2008/0051713 A1 | 2/2008 | Kohlbrenner et al. |

(56) References Cited

U.S. PATENT DOCUMENTS

| | | | |
|---|---|---|---|
| 2008/0228143 A1 | 9/2008 | Stamp | |
| 2008/0228147 A1 | 9/2008 | David-Hegerich et al. | |
| 2008/0262427 A1 | 10/2008 | Hommann | |
| 2008/0262438 A1 | 10/2008 | Bollenbach et al. | |
| 2008/0262443 A1* | 10/2008 | Hommann | A61M 5/2033 604/264 |
| 2009/0012471 A1 | 1/2009 | Harrison | |
| 2009/0012479 A1 | 1/2009 | Moller et al. | |
| 2009/0270804 A1 | 10/2009 | Mesa et al. | |
| 2009/0312705 A1 | 12/2009 | Grunhut et al. | |
| 2010/0137798 A1 | 6/2010 | Streit et al. | |
| 2010/0137801 A1 | 6/2010 | Streit et al. | |
| 2010/0185178 A1 | 7/2010 | Sharp et al. | |
| 2010/0191217 A1 | 7/2010 | Hommann | |
| 2010/0268170 A1 | 10/2010 | Carrel et al. | |
| 2010/0286612 A1 | 11/2010 | Cirillo et al. | |
| 2010/0292653 A1 | 11/2010 | Maritan | |
| 2010/0298780 A1 | 11/2010 | Laiosa | |
| 2011/0077599 A1 | 3/2011 | Wozencroft | |
| 2011/0218500 A1 | 9/2011 | Grunhut et al. | |
| 2012/0010575 A1 | 1/2012 | Jones et al. | |
| 2012/0041387 A1 | 2/2012 | Bruggemann et al. | |
| 2012/0116319 A1* | 5/2012 | Grunhut | A61M 5/3221 604/198 |
| 2012/0172817 A1 | 7/2012 | Bruggemann et al. | |
| 2012/0209192 A1 | 8/2012 | Alexandersson | |
| 2012/0310156 A1 | 12/2012 | Karlsson et al. | |
| 2013/0035647 A1 | 2/2013 | Veasey et al. | |
| 2013/0041328 A1 | 2/2013 | Daniel | |
| 2013/0123710 A1 | 5/2013 | Ekman et al. | |
| 2013/0261556 A1 | 10/2013 | Jones et al. | |
| 2013/0274662 A1 | 10/2013 | Hourmand et al. | |
| 2013/0274677 A1 | 10/2013 | Ekman et al. | |
| 2013/0281942 A1 | 10/2013 | Teucher et al. | |
| 2013/0289525 A1 | 10/2013 | Kemp et al. | |
| 2013/0310739 A1 | 11/2013 | Galbraith et al. | |
| 2013/0310744 A1 | 11/2013 | Brereton et al. | |
| 2013/0310745 A1 | 11/2013 | Latham et al. | |
| 2013/0310757 A1 | 11/2013 | Brereton et al. | |
| 2013/0317427 A1 | 11/2013 | Brereton | |
| 2013/0317428 A1 | 11/2013 | Brereton et al. | |
| 2013/0317479 A1 | 11/2013 | Brereton | |
| 2013/0324925 A1 | 12/2013 | Brereton et al. | |
| 2013/0324939 A1 | 12/2013 | Brereton et al. | |
| 2013/0345643 A1 | 12/2013 | Hourmand et al. | |
| 2014/0336590 A1 | 11/2014 | Hourmand et al. | |
| 2014/0343508 A1 | 11/2014 | Hourmand et al. | |
| 2015/0100029 A1 | 4/2015 | Cowe et al. | |
| 2015/0133872 A1 | 5/2015 | Smith et al. | |
| 2015/0273157 A1 | 10/2015 | Kohlbrenner et al. | |
| 2016/0051767 A1 | 2/2016 | Higgins et al. | |
| 2016/0058950 A1 | 3/2016 | Marsh et al. | |
| 2016/0067415 A1 | 3/2016 | Bayer et al. | |
| 2016/0067418 A1 | 3/2016 | Morris et al. | |
| 2016/0089498 A1 | 3/2016 | Daniel | |
| 2016/0144129 A1 | 5/2016 | Mosebach et al. | |
| 2016/0144133 A1 | 5/2016 | Kemp | |
| 2016/0151585 A1 | 6/2016 | Kemp | |
| 2018/0064875 A1 | 3/2018 | Holmqvist | |

FOREIGN PATENT DOCUMENTS

| | | |
|---|---|---|
| CN | 101264360 | 3/2008 |
| DE | 19819409 | 11/1999 |
| DE | 202007000578 | 3/2007 |
| DE | 102005052502 | 5/2007 |
| DE | 102007013836 | 9/2008 |
| EP | 0666084 | 8/1995 |
| EP | 0693946 | 1/1996 |
| EP | 0824923 | 2/1998 |
| EP | 0991441 | 12/2003 |
| EP | 1932558 | 6/2008 |
| EP | 2080532 | 7/2009 |
| EP | 2399634 | 12/2011 |
| EP | 2468334 | 6/2012 |
| EP | 2468335 | 6/2012 |
| EP | 2606924 | 6/2013 |
| EP | 2606925 | 6/2013 |
| EP | 2675502 | 12/2013 |
| EP | 2705861 | 3/2014 |
| EP | 2946801 | 11/2015 |
| EP | 2753381 | 1/2016 |
| FR | 2990865 | 11/2013 |
| GB | 2438592 | 12/2007 |
| GB | 2461088 | 12/2009 |
| GB | 2469672 | 10/2010 |
| JP | H06-339737 | 12/1994 |
| JP | 2005-177503 | 7/2005 |
| JP | 2007-500530 | 1/2007 |
| JP | 2007-504867 | 3/2007 |
| JP | 2008-528144 | 7/2007 |
| JP | 2008-229344 | 10/2008 |
| JP | 2009-040604 | 2/2009 |
| JP | 2009-040607 | 2/2009 |
| JP | 2009-509605 | 3/2009 |
| JP | 2009-525059 | 7/2009 |
| WO | WO 1996/032974 | 10/1996 |
| WO | WO 1999/053979 | 10/1999 |
| WO | WO 2000/024441 | 5/2000 |
| WO | WO 2000/035060 | 6/2000 |
| WO | WO 2002/047746 | 6/2002 |
| WO | WO 2003/062672 | 7/2003 |
| WO | WO 2004/108194 | 12/2004 |
| WO | WO 2005/097238 | 10/2005 |
| WO | WO 2006/057604 | 6/2006 |
| WO | WO 2007/036676 | 4/2007 |
| WO | WO 2007/066152 | 6/2007 |
| WO | WO 2007/099044 | 9/2007 |
| WO | WO 2007/129324 | 11/2007 |
| WO | WO 2008/059385 | 5/2008 |
| WO | WO 2008/116688 | 10/2008 |
| WO | WO 2009/007305 | 1/2009 |
| WO | WO 2009/040604 | 4/2009 |
| WO | WO 2009/040607 | 4/2009 |
| WO | WO 2009/040672 | 4/2009 |
| WO | WO 2009/062508 | 5/2009 |
| WO | WO 2009/095701 | 8/2009 |
| WO | WO 2010/035059 | 4/2010 |
| WO | WO 2010/035060 | 4/2010 |
| WO | WO 2010/063707 | 6/2010 |
| WO | WO 2011/012903 | 2/2011 |
| WO | WO 2011/109205 | 9/2011 |
| WO | WO 2011/111006 | 9/2011 |
| WO | WO 2011/117592 | 9/2011 |
| WO | WO 2011/126439 | 10/2011 |
| WO | WO 2012/000939 | 1/2012 |
| WO | WO 2012/045350 | 4/2012 |
| WO | WO 2012/085024 | 6/2012 |
| WO | WO 2012/122643 | 9/2012 |
| WO | WO 2013/034647 | 3/2013 |
| WO | WO 2013/034651 | 3/2013 |
| WO | WO 2013/034984 | 3/2013 |
| WO | WO 2013/048310 | 4/2013 |
| WO | WO 2013/077800 | 5/2013 |
| WO | WO 2013/175139 | 11/2013 |
| WO | WO 2013/175144 | 11/2013 |
| WO | WO 2013/175148 | 11/2013 |
| WO | WO 2013/178512 | 12/2013 |
| WO | WO 2014/095424 | 6/2014 |
| WO | WO 2014/154491 | 10/2014 |
| WO | WO 2015/015170 | 2/2015 |
| WO | WO 2015/052224 | 4/2015 |
| WO | WO 2015/071123 | 5/2015 |
| WO | WO 2015/090320 | 6/2015 |
| WO | WO 2015/132234 | 9/2015 |
| WO | WO 2015/144870 | 10/2015 |
| WO | WO 2015/150578 | 10/2015 |
| WO | WO 2015/166286 | 11/2015 |
| WO | WO 2015/169608 | 11/2015 |
| WO | WO 2015/197866 | 12/2015 |
| WO | WO 2016/034407 | 3/2016 |
| WO | WO 2016/041883 | 3/2016 |
| WO | WO 2016/169718 | 10/2016 |

(56) References Cited

FOREIGN PATENT DOCUMENTS

| WO | WO 2016/169719 | 10/2016 |
|---|---|---|
| WO | WO 2016/169756 | 10/2016 |
| WO | WO 2016/176785 | 11/2016 |
| WO | WO 2016/193350 | 12/2016 |
| WO | WO 2016/193622 | 12/2016 |
| WO | WO 2016/202555 | 12/2016 |
| WO | WO 2021/008839 | 1/2021 |

OTHER PUBLICATIONS

International Preliminary Report on Patentability in Application No. PCT/EP2012/052648, dated Aug. 21, 2013, 6 pages.
International Preliminary Report on Patentability in International Application No. PCT/EP2011/060726, dated Dec. 28, 2012, 6 pages.
International Preliminary Report on Patentability in International No. PCT/EP2012/052642, dated Aug. 21, 2013, 7 pages.
International Search Report and Written Opinion in Application No. GB0906973.3, dated Aug. 26, 2009, 2 pages.
International Search Report and Written Opinion in Application No. PCT/EP2012/052639, dated May 11, 2012, 9 pages.
International Search Report and Written Opinion in Application No. PCT/EP2012/052640, dated May 14, 2012, 8 pages.
International Search Report and Written Opinion in Application No. PCT/EP2012/052646, dated Nov. 5, 2012, 9 pages.
International Search Report and Written Opinion in Application No. PCT/EP2012/052647, dated May 8, 2012, 10 pages.
International Search Report and Written Opinion in Application No. PCT/EP2012/052648, dated May 18, 2012, 8 pages.
International Search Report and Written Opinion in Application No. PCT/EP2012/059758, dated Aug. 13, 2012, 12 pages.
International Search Report and Written Opinion in Application No. PCT/EP2013/052653, dated May 11, 2012, 10 pages.
International Search Report and Written Opinion in International Application No. PCT/EP2011/060726, dated Aug. 31, 2011, 9 pages.
International Search Report and Written Opinion in International Application No. PCT/EP2012/052642, dated May 18, 2012, 11 pages.
International Search Report and Written Opinion in International Application No. PCT/EP2012/0526943, dated May 8, 2012, 10 pages.
International Search Report in Application No. PCT/EP2012/052643, dated Apr. 25, 2012, 3 pages.
International Search Report in Application No. PCT/EP2012/052652, dated May 10, 2012, 4 pages.
International Search Report in Application No. PCT/EP2012/052653, dated May 11, 2012, 3 pages.
International Search Report in Application No. PCT/SE99/01922, dated Mar. 28, 2000, 6 pages.
Japanese Office Action in Application No. 2013-517229, dated Jun. 9, 2015, 5 pages.
Japanese Office Action in Application No. 2013-553926, dated Jan. 5, 2016, 4 pages, English translation only.
Japanese Office Action in Application No. 2013-553927, dated Feb. 2, 2016, 5 pages.
Japanese Office Action in Application No. 2013-553931, dated Dec. 15, 2015, 5 pages, English translation only.
Japanese Office Action in Japanese Application No. 2013-553936, dated Dec. 22, 2015, 4 pages.
Merriam-Webster Dictionary, 2015, Simple Definition, 1 page.
Office Action in U.S. Appl. No. 13/983,807, dated Dec. 24, 2015, 16 pages.
Office Action in U.S. Appl. No. 13/983,807, dated Jul. 28, 2015, 20 pages.
Office Action in U.S. Appl. No. 13/983,807, dated Oct. 21, 2016, 10 pages.
Office Action in U.S. Appl. No. 13/983,809, dated Mar. 28, 2016, 14 pages.
Office Action in U.S. Appl. No. 13/983,809, dated Sep. 27, 2016, 8 pages.
Office Action in U.S. Appl. No. 13/984,849, dated Jul. 26, 2016, 11 pages.
Office Action in U.S. Appl. No. 13/985,021, dated Jul. 26, 2016, 10 pages.
Office Action in U.S. Appl. No. 14/000,113, dated Mar. 19, 2015, 21 pages.
Russian Office Action in Application No. 2013/142343/14, dated Dec. 28, 2015, 6 pages, with English translation.
Russian Office Action in Application No. 2013/142356/14, dated Dec. 28, 2015, 6 pages, with English translation.
Russian Office Action in Application No. 2013/142356/14, dated Sep. 17, 2013, 6 pages.
Taiwan Search Report in Application No. 101105003, dated Nov. 5, 2015, 1 page.
Taiwan Search Report in Application No. 101105004, dated Nov. 3, 2015, 1 page.
Taiwan Search Report in Application No. 101105007, dated Oct. 22, 2015, 1 page.
Taiwan Search Report in Application No. 101105009, dated Oct. 31, 2015, 1 page.
Taiwan Search Report in Application No. 101105011, dated Oct. 31, 2015, 1 page.

\* cited by examiner

AUTO-INJECTOR

CROSS REFERENCE TO RELATED APPLICATIONS

The present application is a continuation of U.S. patent application Ser. No. 17/719,441, filed on Apr. 13, 2022, which is a continuation of U.S. patent application Ser. No. 16/809,669, filed on Mar. 5, 2020, now U.S. Pat. No. 11,311,671, which is a continuation of U.S. patent application Ser. No. 15/880,251, filed on Jan. 25, 2018, now U.S. Pat. No. 10,603,436, which is a continuation of U.S. patent application Ser. No. 15/165,720, filed on May 26, 2016, now U.S. Pat. No. 9,931,471, which is a continuation of U.S. patent application Ser. No. 13/806,324, filed on Dec. 21, 2012, now U.S. Pat. No. 9,352,088, which is a U.S. National Phase Application pursuant to 35 U.S.C. § 371 of International Application No. PCT/EP2011/060726, filed on Jun. 27, 2011, which claims priority to European Patent Application No. 10167506.4, filed on Jun. 28, 2010. The entire disclosure contents of these applications are herewith incorporated by reference into the present application.

TECHNICAL FIELD

The invention relates to an auto-injector for administering a dose of a liquid medicament according to the preamble of claim 1.

BACKGROUND

Administering an injection is a process which presents a number of risks and challenges for users and healthcare professionals, both mental and physical.

Injection devices (i.e. devices capable of delivering medicaments from a medication container) typically fall into two categories—manual devices and auto-injectors.

In a manual device—the user must provide the mechanical energy to drive the fluid through the needle. This is typically done by some form of button/plunger that has to be continuously pressed by the user during the injection. There are numerous disadvantages to the user from this approach. If the user stops pressing the button/plunger then the injection will also stop. This means that the user can deliver an underdose if the device is not used properly (i.e. the plunger is not fully pressed to its end position). Injection forces may be too high for the user, in particular if the patient is elderly or has dexterity problems.

The extension of the button/plunger may be too great. Thus it can be inconvenient for the user to reach a fully extended button. The combination of injection force and button extension can cause trembling/shaking of the hand which in turn increases discomfort as the inserted needle moves.

Auto-injector devices aim to make self-administration of injected therapies easier for patients. Current therapies delivered by means of self-administered injections include drugs for diabetes (both insulin and newer GLP-1 class drugs), migraine, hormone therapies, anticoagulants etc.

Auto-injectors are devices which completely or partially replace activities involved in parenteral drug delivery from standard syringes. These activities may include removal of a protective syringe cap, insertion of a needle into a patient's skin, injection of the medicament, removal of the needle, shielding of the needle and preventing reuse of the device. This overcomes many of the disadvantages of manual devices. Injection forces/button extension, hand-shaking and the likelihood of delivering an incomplete dose are reduced. Triggering may be performed by numerous means, for example a trigger button or the action of the needle reaching its injection depth. In some devices the energy to deliver the fluid is provided by a spring.

US 2002/0095120 A1 discloses an automatic injection device which automatically injects a pre-measured quantity of fluid medicine when a tension spring is released. The tension spring moves an ampoule and the injection needle from a storage position to a deployed position when it is released. The content of the ampoule is thereafter expelled by the tension spring forcing a piston forward inside the ampoule. After the fluid medicine has been injected, torsion stored in the tension spring is released and the injection needle is automatically retracted back to its original storage position.

The spring means is a single compression spring arranged to be grounded at a distal end in the housing for advancing the needle and for injecting the dose of medicament via a plunger and wherein the compression spring is arranged to have its ground in the housing switched to its proximal end for retracting the syringe.

SUMMARY

It is an object of the present invention to provide an improved auto-injector.

The object is achieved by an auto-injector according to claim 1.

Preferred embodiments of the invention are given in the dependent claims.

In the context of this specification the term proximal refers to the direction pointing towards the patient during an injection while the term distal refers to the opposite direction pointing away from the patient.

According to the invention, an auto-injector for administering a dose of a liquid medicament comprises:

an elongate housing arranged to contain a syringe with a hollow needle and a stopper for sealing the syringe and displacing the medicament, the housing having a distal end and a proximal end with an orifice intended to be applied against an injection site, wherein the syringe is slidably arranged with respect to the housing, spring means capable of, upon activation:

pushing the needle from a covered position inside the housing into an advanced position through the orifice and past the proximal end, operating the syringe to supply the dose of medicament, and retracting the syringe with the needle into the covered position after delivering the medicament, activating means arranged to lock the spring means in a pressurized state prior to manual operation and capable of, upon manual operation, releasing the spring means for injection.

According to the invention the spring means is a single drive spring in the shape of a compression spring arranged to be grounded at a distal end in the housing for advancing the needle and for injecting the dose of medicament. The force of the drive spring is forwarded to the needle and/or the syringe via a plunger. The drive spring is arranged to have its ground in the housing switched to its proximal end for retracting the syringe when the injection of the medicament is at least nearly finished.

The single drive spring is used for inserting the needle, fully emptying the syringe and retracting the syringe and needle to a safe position after injection. Thus a second spring for withdrawing the syringe and needle, which is a motion with an opposite sense compared to advancing the syringe and injecting the dose, is not required. While the distal end of the drive spring is grounded the proximal end moves the syringe forward for inserting the needle and carries on to the injection by pushing on the stopper. When the injection is at least nearly finished the drive spring bottoms out at its proximal end, resulting in the proximal end being grounded in the housing. At the same time the distal end of the drive spring is released from its ground in the housing. The drive spring is now pulling the syringe in the opposite direction.

According to the invention the activating means is arranged as a trigger button laterally arranged on the housing. A lateral trigger button can be easier to operate for people with dexterity problems.

The auto-injector according to the invention has a particularly low part count compared to most conventional auto-injectors. The use of just one drive spring reduces the amount of metal needed and thus consequently reduces weight and manufacturing costs.

The trigger button is preferably pivoted in the housing and arranged to be rotated when operated.

An interlock sleeve may be telescoped in the proximal end of the housing, the interlock sleeve translatable in longitudinal direction between a proximal position and a distal position and biased in proximal direction in a manner to protrude from the housing in the proximal position. The interlock sleeve is arranged to be translated from its proximal position into an intermediate position when pressed against the injection site. The trigger button is arranged to push the interlock sleeve from the intermediate position into the distal position thus releasing the drive spring. Before the syringe and needle translate in proximal direction the activating means, i.e. the lateral trigger button has to be operated so as to release the drive spring. The probability for inadvertent operation of the auto-injector thus decreases due to the requirement of two user actions, pressing the auto-injector against the injection site and operating the trigger button.

In its proximal position the interlock sleeve may be arranged to hold the trigger button in a depressed position, e.g. flush with the housing. Translation of the interlock sleeve into the intermediate position causes the trigger button to emerge from the housing into a ready position. This provides a sequenced operation in a manner that the trigger button cannot be operated before the interlock sleeve is pressed against the injection site.

It is desirable to trigger the retraction of the needle when the contents of the syringe have been entirely delivered to the patient, i.e. when the stopper has bottomed out in the syringe. Automatically triggering the retraction when the stopper exactly reaches the end of its travel is a problem due to tolerances when manufacturing the syringe and stopper. Due to these tolerances the position of the stopper at the end of its travel relative to the retracting means is not repeatable. Consequently, in some cases the stopper would prematurely bottom out so the retraction would not be triggered at all. In other cases the retraction would be triggered before the stopper bottomed so residual medicament would remain in the syringe.

The retraction could automatically be triggered a certain amount of time or travel before the stopper bottoms out in the syringe. However this reliable retraction would be traded off for residual medicament in the syringe.

Thus, in a preferred embodiment the interlock sleeve is furthermore arranged to prevent release of the distal ground of the drive spring when in its intermediate and/or distal position. This means, the drive spring remains distally grounded as long as the auto-injector is kept pressed against the injection site so the needle retraction can only start when the auto-injector is removed from the injection site and the interlock sleeve consequently returns into its proximal position and thus releases the distal ground.

A retraction sleeve may be axially movable arranged in the housing, wherein the drive spring is arranged inside the retraction sleeve with its distal end bearing against a distal end face and with its proximal end bearing against a thrust face of a decoupling member. A resilient lug on the interlock sleeve is arranged to be engaged with the retraction sleeve by the trigger button being depressed when the interlock sleeve is in its intermediate or distal position so as to prevent the retraction sleeve from translating in distal direction. Thus, when the interlock sleeve is pressed against the injection site, the retraction sleeve is kept from retracting. Only after removal of the auto-injector from the injection site and consequent translation of the interlock sleeve into its proximal position the retraction sleeve may translate in distal direction and retract the needle into the housing.

The lug may be engaged between two ramps on the trigger button in such a manner that the trigger button is pulled into the depressed position upon translation of the interlock sleeve into its proximal position by the lug sliding along the first ramp. The trigger button is pushed into its ready position by the lug sliding along the second ramp.

A third ramp may be arranged on the interlock sleeve for being engaged by a pin on the trigger button when the trigger button is being pressed when the interlock sleeve is in its intermediate position. When the trigger button is being pressed the pin slides along the third ramp and translates the interlock sleeve into its distal position for triggering the injection.

A tubular syringe carrier may be arranged for holding the syringe and supporting it at its proximal end. Supporting the syringe at the proximal end is preferred over support at the finger flanges since the finger flanges are more frangible under load while the proximal or front end of the syringe is more robust. The syringe and the syringe carrier are arranged for joint axial translation. The syringe carrier is telescoped in the interlock sleeve.

In a preferred embodiment at least one latch is provided for axially fixing the retraction sleeve in a maximum proximal position. The decoupling member is arranged to decouple the latch when being moved in proximal direction nearly into a maximum proximal position. When decoupled, the retraction sleeve is allowed to move in distal direction and retract the needle by means of the spring force which is no longer grounded at its distal end. Thus, retraction can only occur if the latches have been released and if the auto-injector has been removed from the injection site.

Preferably the plunger is arranged for pushing the syringe and/or the stopper in proximal direction. At least one but preferably two or more resilient decoupling arms are arranged at the decoupling member. The decoupling arms exhibit inner ramped surfaces bearing against a first shoulder of the plunger in proximal direction. The resilient decoupling arms are supportable by an inner wall of the retraction sleeve in order to prevent the decoupling arms from being flexed outward and slip past the first shoulder. In this state the plunger may be pushed in proximal direction by the decoupling member pushing against the first shoulder in order to insert the needle and inject the dose. At least one aperture is arranged in the retraction sleeve allowing the decoupling arms to be flexed outward by the first shoulder thus allowing the first shoulder to slip through the decoupling arms in proximal direction. This may happen when the injection is at least nearly finished. The decoupled plunger allows the syringe and needle to be retracted since it is no longer bearing against the decoupling member.

The syringe may be arranged for joint axial movement with a syringe holder which is slidably arranged in the retraction sleeve. The syringe holder is provided with at least two resilient syringe holder arms arranged distally, the syringe holder arms having a respective inclined surface for bearing against a second shoulder, which is arranged at the plunger proximally from the first shoulder. The syringe holder arms are supportable by an inner surface of the housing in order to prevent them from being flexed outward. Thus, when the trigger button is pressed the spring force forwarded by the plunger does not yet press against the stopper but against the syringe for forwarding it. Consequently, a so called wet injection is avoided, i.e. the liquid medicament is not leaking out of the hollow needle before the needle is inserted. A widened portion is provided in the housing for allowing the syringe holder arms to flex outwards when the syringe holder has nearly reached a maximum proximal position thus allowing the second shoulder to slip through the syringe holder arms and to switch load of the drive spring from the syringe to the stopper. This allows for defining the moment to start injecting the medicament.

The syringe holder may have at least one stop for being engaged by a resilient first clip on the housing in a manner to prevent translation of the syringe holder in proximal direction. The first clip may be arranged to decouple from the stop upon translation of the interlock sleeve into its distal position in order to release the drive spring and start the injection.

Usually the hollow needle is equipped with a protective needle shield for keeping the needle sterile and preventing it from being mechanically damaged. The protective needle shield is attached to the needle when the auto-injector or the syringe is assembled.

Preferably a cap is provided at the proximal end of the housing. A sheet metal clip is attached to the cap for joint axial movement and independent rotation. The sheet metal clip is arranged to extend through an orifice into the interlock sleeve when the cap is attached to the interlock sleeve. The sheet metal clip incorporates at least two barbs snapped into a circumferential notch or behind a shoulder of the protective needle shield. This allows for automatically engaging the sheet metal clip with the protective needle shield during assembly. When the cap is removed from the interlock sleeve in preparation of an injection the protective needle shield is reliably removed without exposing the user too high a risk to injure themselves.

The cap may be attachable to the housing by a screw connection. This allows for a low force removal of the protective needle shield.

The housing may have at least one viewing window for inspecting the syringe.

The auto-injector may preferably be used for subcutaneous or intra-muscular injection, particularly for delivering one of an analgetic, an anticoagulant, insulin, an insulin derivate, heparin, Lovenox, a vaccine, a growth hormone, a peptide hormone, a proteine, antibodies and complex carbohydrates.

The cap with the sheet metal spring may also be applied with other auto-injectors and injection devices.

Further scope of applicability of the present invention will become apparent from the detailed description given hereinafter. However, it should be understood that the detailed description and specific examples, while indicating preferred embodiments of the invention, are given by way of illustration only, since various changes and modifications within the spirit and scope of the invention will become apparent to those skilled in the art from this detailed description.

BRIEF DESCRIPTION OF THE DRAWINGS

The present invention will become more fully understood from the detailed description given hereinbelow and the accompanying drawings which are given by way of illustration only, and thus, are not limitive of the present invention, and wherein.

Corresponding parts are marked with the same reference symbols in all figures.

DETAILED DESCRIPTION

Figure 1A:
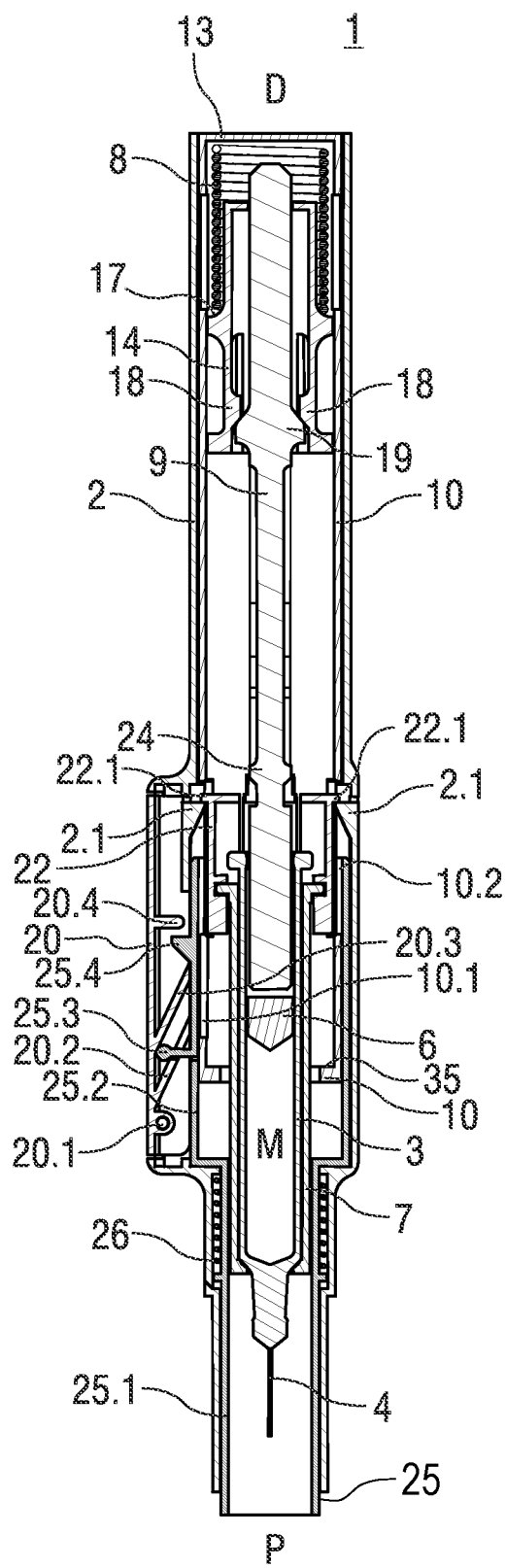
FIGS. 1A-B are two longitudinal sections of an auto-injector with a single drive spring for advancing a syringe with a needle, injecting a dose of medicament and retracting the syringe and needle, the auto-injector as-delivered.
Figure 1B:
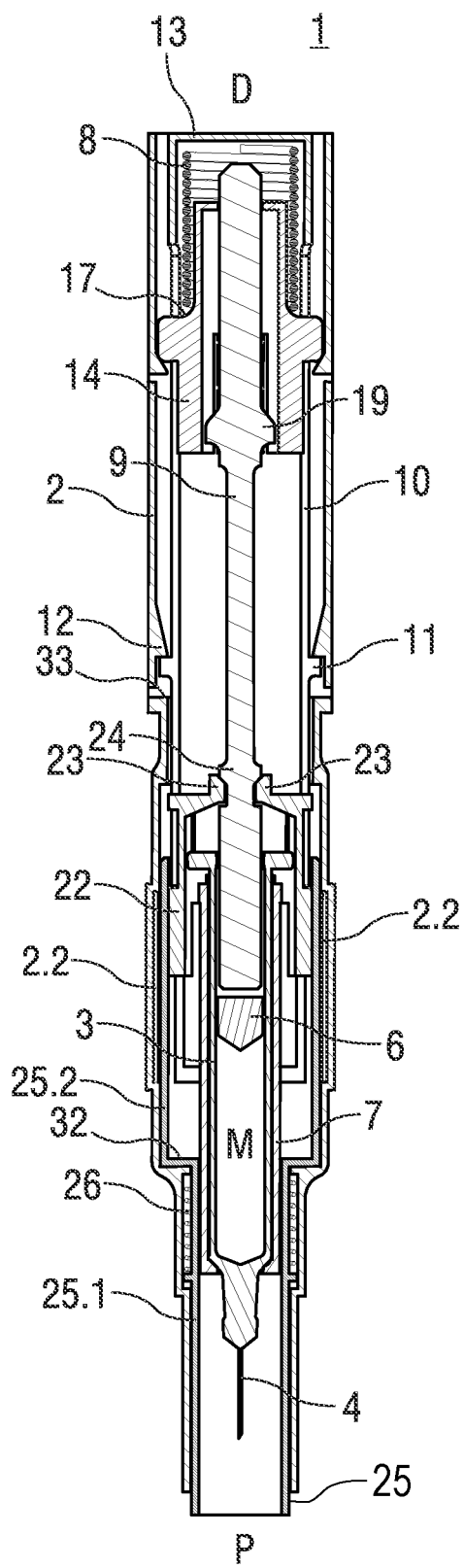

FIGS. 1A-B show two longitudinal sections in different section planes of an auto-injector 1, the different section planes approximately 90° rotated to each other. The auto-injector 1 comprises an elongate housing 2. A syringe 3, e.g. a Hypak syringe, with a hollow needle 4 is arranged in a proximal part of the auto-injector 1. When the auto-injector 1 or the syringe 3 is assembled a protective needle shield may be attached to the needle (not illustrated). A stopper 6 is arranged for sealing the syringe 3 distally and for displacing a liquid medicament M through the hollow needle 4. The syringe 3 is held in a tubular syringe carrier 7 and supported at its proximal end therein. A single drive spring 8 in the shape of a compression spring is arranged in a distal part of the auto-injector 1. A plunger 9 is arranged for forwarding the spring force of the drive spring 8.

Inside the housing 2 a retraction sleeve 10 is slidably arranged. Before the injection is triggered the retraction sleeve 10 is in a maximum proximal position and prevented from moving in distal direction D by means of stops 11 caught behind latches 12 in the housing 2. A distal end of the drive spring 8 bears against an end face 13 of the retraction sleeve 10. Due to the stops 11 and latches 12 the force of the drive spring 8 is reacted into the housing 2. The proximal end of the drive spring 8 bears against a decoupling member 14 arranged around the plunger 9.

The decoupling member 14 comprises a thrust face 17 for bearing against a proximal end of the drive spring 8. Proximally from the thrust face 17 two or more resilient decoupling arms 18 are provided at the decoupling member 14, the decoupling arms 18 having inner ramped surfaces bearing against a first shoulder 19 in the plunger 9 in proximal direction P. The resilient decoupling arms 18 are supported by an inner wall of the retraction sleeve 10 in this situation so they cannot flex outward and slip past the first shoulder 19.

The syringe carrier 7 is engaged for joint axial movement with a syringe holder 22 which is slidably arranged in the retraction sleeve 10. The syringe holder 22 is provided with two or more resilient syringe holder arms 23 arranged distally. The syringe holder arms 23 have a respective inclined surface for bearing against a second shoulder 24 in the plunger 9 arranged proximally from the first shoulder 19. In the initial position shown in FIGS. 1A-B the syringe holder arms 23 are supported by an inner surface (not illustrated) of the housing 2 so they cannot flex outward and the second shoulder 24 cannot slip through. In order to support the syringe holder arms 23 at the housing 2 a respective number of apertures are provided in the retraction sleeve 10.

Two resilient first clips 2.1 are arranged in the housing 2 which engage stops 22.1 on the syringe holder 22 so as to prevent translation of the syringe holder 22, the syringe carrier 7, the syringe 3 and the needle 4 in proximal direction P. Since the syringe holder arms 23 are kept from flexing out, the load of the drive spring 8 is statically resolved through the decoupling member 14, the plunger 9 and the syringe holder 22 into the first clips 2.1 in the housing 2.

A lateral trigger button 20 is arranged laterally on the housing 2 with a pivot 20.1 near its proximal end. In the as delivered configuration in FIGS. 1A-B the trigger button 20 is flush with the housing 2 so it cannot be depressed.

A skin interlock sleeve 25 is telescoped in the proximal end P of the housing 2. An interlock spring 26 for biasing the interlock sleeve 25 in proximal direction P is arranged between the housing 2 and the interlock sleeve 25. The syringe carrier 7 is telescoped in a proximal portion 25.1 of the interlock sleeve 25. A distal portion 25.2 of the interlock sleeve 25 has a greater diameter than the proximal portion 25.1. The syringe holder 22 is telescoped in the distal portion 25.2. The distal portion 25.2 exhibits a lug 25.3 and a third ramp 25.4 for interacting with the trigger button 20. The lug 25.3 is caught between two ramps 20.2, 20.3 arranged inwardly in the trigger button 20.

In order to start an injection the proximal end P of the auto-injector 1 has to be pressed against the injection site, e.g. a patient's skin. As a result the interlock sleeve 25 translates in distal direction D into the housing 2 (see FIG. 2) until the interlock sleeve 25 is flush with the proximal end P of the housing 2. The lug 25.3 also moves in distal direction D along the second ramp 20.3 of the trigger button 20 thus rotating the trigger button outwardly in such a manner that the trigger button 20 laterally emerges from the housing 2 (see FIG. 2).

The trigger button 20 has now been moved to a position where if pushed it will release the drive spring 8 in order to insert the needle 4 into the injection site and to inject the medicament M.

If the auto-injector 1 is removed from the injection site without operating the trigger button 20 the interlock sleeve 25 will translate back into its proximal position under load of the interlock spring 26. The lug 25.3 will slide along the first ramp 20.2 and pull the trigger button 20 back into the position as in FIGS. 1A-B.

The lug 25.3 is resiliently arranged in the interlock sleeve 25 in such a manner that it may be pushed radially inwards. As long as the interlock sleeve 25 is in its proximal position as in FIGS. 1A-B the lug 25.3 is prevented from flexing inwards by the retraction sleeve 10. When the interlock sleeve 25 is pushed into the housing 2 as in FIG. 2 the lug 25.3 reaches an aperture 10.1 in the retraction sleeve 10 allowing it to flex inwards. If the interlock sleeve 25 is kept pressed against the injection site and the trigger button 20 is being depressed the lug 25.3 will be pushed inwards through the aperture 10.1. The resilience of the lug 25.3 has to be chosen so as to ensure that the force required to keep the interlock sleeve 25 pressed does not exceed a convenient level for the user since the counteracting force is the sum of the spring force of the interlock spring 26 and the force created by the lug 25.3 trying to slide along the second ramp 20.3.

When the lug 25.3 has entered the aperture 10.1 the skin interlock sleeve 25 is prevented from returning into its proximal position.

If the trigger button 20 was depressed with the interlock sleeve 25 only partially translated into the housing 2 the lug 25.3 would not yet have reached the aperture 10.1 so it could not flex inwards. Instead, depressing the trigger button 20 would force the interlock sleeve 25 back into its proximal position due to the engagement of the lug 25.3 with the second ramp 20.3.

Figure 2:
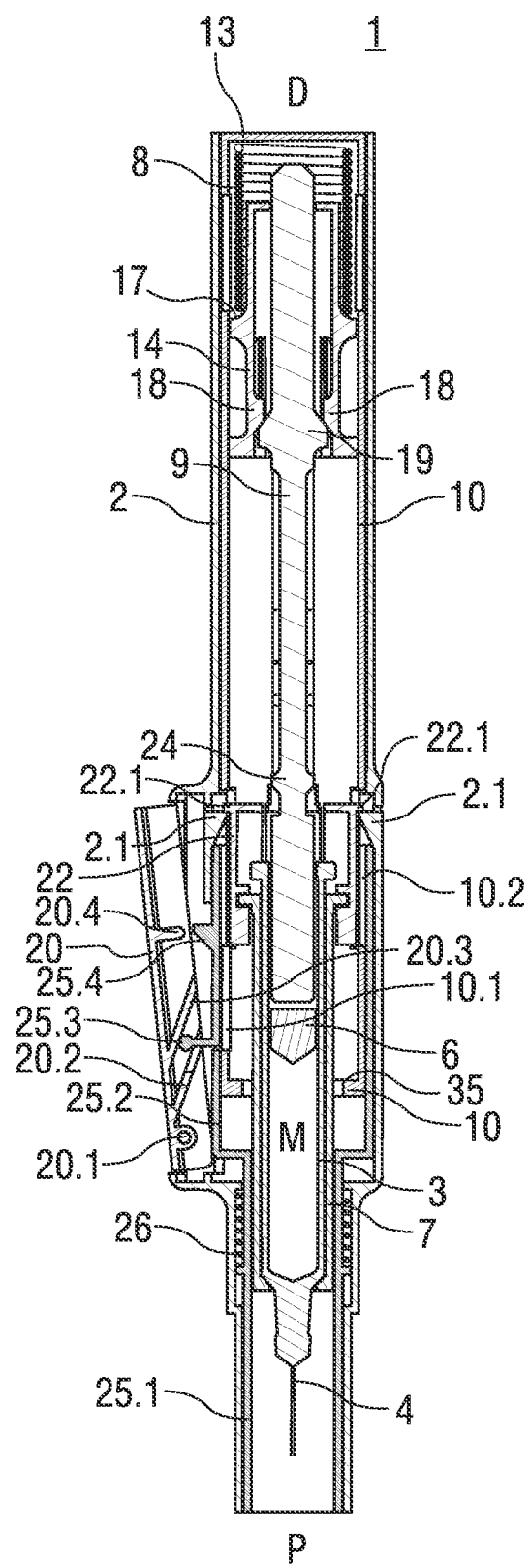
FIG. 2 is a longitudinal section of the auto-injector with a skin interlock sleeve translated in distal direction and a lateral trigger button ready to be operated.
Figure 3:
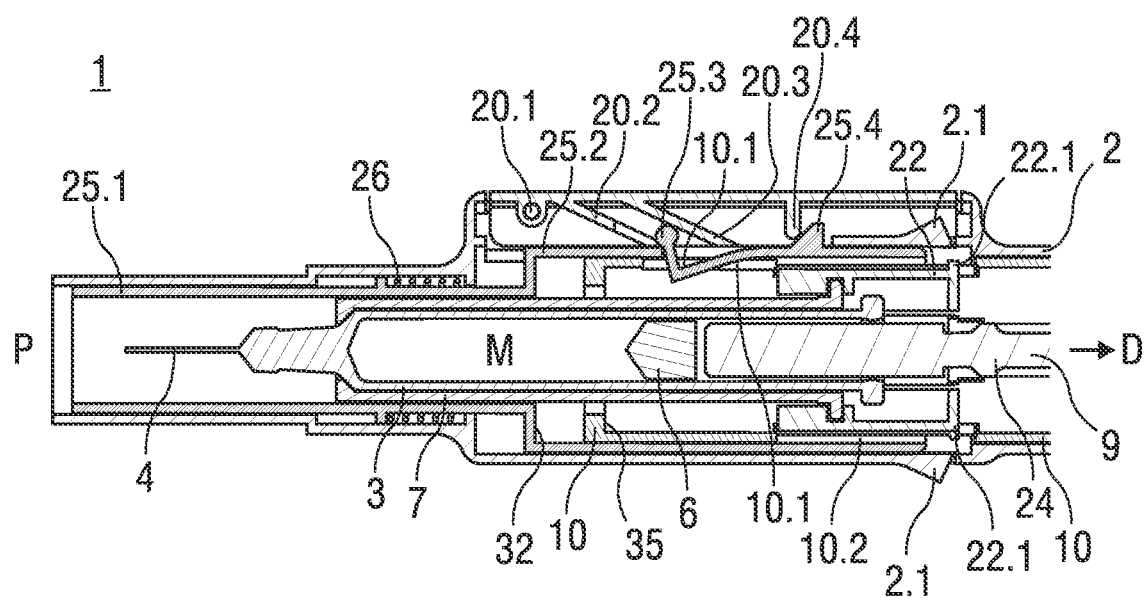
FIG. 3 is a detail of the auto-injector with the trigger button depressed.

When the trigger button 20 is pushed in the situation shown in FIG. 2, the lug 25.3 is pushed radially inwards. A pin 20.4, inwardly arranged on the trigger button 20, is pressed against the third ramp 25.4 in such a manner that the interlock sleeve 25 is translated further in distal direction D into the housing 2, as shown in FIG. 3. This movement will result in a further flexing of the lug 25.3, as it slides along the second ramp 20.3. This position cannot be reached by just pushing the interlock sleeve 25 against the injection site. A distal end of the distal portion 25.2 now reaches the clips 2.1 and pushes them outwards thus decoupling the syringe holder 22 from the housing 2 and releasing the drive spring 8.

The second shoulder 24 pushes the syringe holder 22, syringe carrier 7 and syringe 3 forward in proximal direction P while no load is exerted onto the stopper 6. The hollow needle 4 appears from the proximal end P and is inserted into the injection site.

The forward movement continues until the syringe holder 22 bottoms out at a front face 35 of the retraction sleeve 10. The travel from the initial position up to this point defines an injection depth, i.e. needle insertion depth.

When the syringe holder 22 has nearly bottomed out, the resilient syringe holder arms 23 have reached a widened portion 2.2 of the housing 2 where they are no longer supported by the inner wall of the housing 2. However, since the force required to insert the needle 4 is relatively low the second shoulder 24 will continue to drive forward the syringe holder 22 until proximal travel is halted at the front face 35. At this point the syringe holder arms 23 are flexed out by the continued force of the second shoulder 24 and allow it to slip through. Now the plunger 9 no longer pushes against the syringe holder 22 but against the stopper 6 for expelling the medicament M from the syringe 3 and injecting it into or through the patient's skin.

When the stopper 6 has nearly bottomed out in the syringe 3 the decoupling member 14 has reached a position where it pushes against the latches 12 in a manner to decouple the retraction sleeve 10 from the housing 2. Thus the drive spring 8 is no longer grounded with its distal end in the housing 2 by the latches 12. Instead, as soon as the decoupling member 14 has bottomed out at a second abutment 33 in the housing 2 the proximal end of the drive spring 8 gets grounded in the housing 2 while its distal end is pulling the retraction sleeve 10 in distal direction D.

Just before the decoupling member 14 decouples the retraction sleeve 10 from the housing 2 the decoupling arms 18 reach an aperture 10.1, 10.2 in the retraction sleeve 10 so they are no longer kept from being flexed outward. The decoupling arms 18 are thus pushed outward by the first shoulder 19 pushing against its ramped surfaces so the first shoulder 19 can slip through in distal direction D as soon as the decoupling member 14 has hit the second abutment 33.

Although the latches 12 are disengaged now, the retraction sleeve 10 may not yet slide in distal direction D because of the lug 25.3 engaged in the aperture 10.1 so the retraction sleeve 10 is trying to pull the interlock sleeve 25 in distal direction D which is prevented by the third ramp 25.4 distally abutting against the housing 2.

If the auto-injector 1 is taken away from the injection site and the user releases the trigger button 20 the lug 25.3 re-emerges from inside the retraction sleeve 10 so the retraction sleeve 10 gets disengaged from the interlock sleeve 25 and may now translate in distal direction D. A spring means may be arranged for actively pulling the trigger button 20 outwards in this situation. In an alternative embodiment the lug 25.3 may project outwards with an inclination in proximal direction P so as to allow the retraction sleeve 10 to push it outwards on retraction.

The syringe holder 22 is taken along in distal direction D by the retraction sleeve 10, e.g. by a front face 35. Thus the syringe 3 and needle 4 are retracted into a safe position inside the housing 2, e.g. into the initial position. The plunger 9, no longer bearing against the decoupling arms 18 is pulled back, too.

The housing 2 may have at least one viewing window for inspecting the syringe 3.

The auto-injector 1 may preferably be used for subcutaneous or intra-muscular injection, particularly for delivering one of an analgesic, an anticoagulant, insulin, an insulin derivate, heparin, Lovenox, a vaccine, a growth hormone, a peptide hormone, a protein, antibodies and complex carbohydrates.

The invention claimed is:

1. An auto-injector comprising:
a housing having at least one viewing window for viewing a syringe disposed within the housing;
a first part movably disposed relative to the housing and comprising a first surface and a second surface axially spaced apart from each other, the first part configured to move relative to the housing to initiate an injection of a medicament from the syringe;
a second part slidably disposed relative to the first part and comprising
a first proximally-extending resilient arm with an outward protrusion configured to engage the first surface of the first part such that movement of the first part causes movement of the second part,
a first ramped portion configured to engage the second surface of the first part to cause inward deflection of the first proximally-extending resilient arm when the first ramped portion and the second surface move axially relative to each other, and
a second portion configured to engage a second resilient arm of the auto-injector such that the second resilient arm outwardly deflects relative to the second part to release a plunger rod of the auto-injector from being held in a distal position within the housing such that the plunger rod moves proximally relative to the housing under a proximally-directed biasing force of a drive spring of the auto-injector to dispense the medicament from the syringe;
a sleeve at least partially disposed within the second part and comprising
an outer surface configured to engage an inner surface of a portion of the first proximally-extending resilient arm to prevent inward deflection of the first proximally-extending resilient arm from a relaxed position to a deflected position when the sleeve and the second part are in a first position relative to each other,
an opening defined by the outer surface shaped and sized to receive the portion of the first proximally-extending resilient arm to allow inward deflection of the first proximally-extending resilient arm from the relaxed position to the deflected position and into the opening when the sleeve and the second part are in a second position relative to each other, the second part and the sleeve configured to move axially relative to each other from the first position to the second position, and
an outward protrusion configured to couple the sleeve to the housing to limit axial movement of the sleeve relative to the housing, the outward protrusion being proximal of the opening; and
a syringe carrier disposed within the housing and comprising a proximal portion configured to engage a proximal necked portion of the syringe to limit proximal movement of the syringe relative to the syringe carrier.

2. The auto-injector of claim 1, wherein the auto-injector is configured such that distal movement of a proximal end of the auto-injector causes a needle sleeve spring to compress, the first part to move relative to the housing, and the second part to move relative to the housing.

3. The auto-injector of claim 2, wherein the needle sleeve spring is disposed between the second part and the housing.

4. The auto-injector of claim 3, wherein the proximal end of the auto-injector is configured to contact a body of a user and move distally relative to the housing when pressed against the body of the user.

5. The auto-injector of claim 1, wherein an axial end of the sleeve is configured to be coupled to the syringe to bias the syringe in an axial direction.

6. The auto-injector of claim 1, wherein a distal end of the syringe carrier comprises an outward portion configured to at least partially retain the syringe carrier within to the housing.

7. The auto-injector of claim 6, wherein a distal end of the syringe comprises a distal flange that is distally spaced apart from the outward portion of the syringe carrier.

8. The auto-injector of claim 1, comprising a third part comprising a third proximally-extending resilient arm configured to releasably engage a surface of the plunger rod to releasably couple proximal movement between the third part and the plunger rod as the plunger rod moves proximally relative to the housing to dispense the medicament from the syringe.

9. The auto-injector of claim 8, wherein the third proximally-extending resilient arm is configured to releasably couple proximal movement between the third part and the plunger rod such that (i) the third part and the plunger rod proximally move together for a first distance as the plunger rod moves proximally relative to the housing to dispense the medicament from the syringe and (ii) the third part is decoupled from the plunger rod for a second distance as the plunger rod moves proximally relative to the housing to dispense the medicament from the syringe.

10. An auto-injector comprising:
a housing having at least one viewing window for viewing a syringe disposed within the housing;
a first part movably disposed relative to the housing and comprising a first surface and a second surface axially spaced apart from each other;

a second part slidably disposed relative to the first part and comprising
  a first proximally-extending resilient arm with an outward protrusion configured to engage the first surface of the first part such that movement of the first part causes movement of the second part,
  a first ramped portion configured to engage the second surface of the first part to cause inward deflection of the first proximally-extending resilient arm when the first ramped portion and the second surface move axially relative to each other, and
  a second portion configured to engage a second resilient arm of the auto-injector such that the second resilient arm outwardly deflects relative to the second part to release a plunger rod of the auto-injector from being held in a distal position within the housing such that the plunger rod moves proximally relative to the housing under a proximally-directed biasing force of a drive spring of the auto-injector to dispense the medicament from the syringe; and
a sleeve at least partially disposed within the second part and configured to (i) prevent inward deflection of the first proximally-extending resilient arm when the sleeve and the second part are in a first position relative to each other and (ii) allow inward deflection of the first proximally-extending resilient arm when the sleeve and the second part are in a second position relative to each other, the second part and the sleeve configured to move axially relative to each other from the first position to the second position.

11. The auto-injector of claim 10, comprising a syringe carrier disposed within the housing and comprising a proximal portion configured to engage a proximal necked portion of the syringe to limit proximal movement of the syringe relative to the syringe carrier, and an outward portion configured to at least partially retain the syringe carrier within to the housing.

12. The auto-injector of claim 11, wherein a distal end of the syringe comprises a distal flange that is distally spaced apart from the outward portion of the syringe carrier and the syringe contains the medicament.

13. The auto-injector of claim 10, wherein the auto-injector is configured such that distal movement of a proximal end of the auto-injector causes a needle sleeve spring to compress, the first part to move relative to the housing, and the second part to move relative to the housing, the needle sleeve spring being disposed between the second part and the housing.

14. The auto-injector of claim 10, comprising a third part comprising a third proximally-extending resilient arm configured to releasably engage a surface of the plunger rod to releasably couple proximal movement between the third part and the plunger rod as the plunger rod moves proximally relative to the housing to dispense the medicament from the syringe.

15. The auto-injector of claim 14, wherein the third proximally-extending resilient arm is configured to releasably couple proximal movement between the third part and the plunger rod such that (i) the third part and the plunger rod proximally move together for a first distance as the plunger rod moves proximally relative to the housing to dispense the medicament from the syringe and (ii) the third part is decoupled from the plunger rod for a second distance as the plunger rod moves proximally relative to the housing to dispense the medicament from the syringe.

16. An auto-injector comprising:
a housing having at least one viewing window for viewing a syringe disposed within the housing; and
a first part movably disposed relative to the housing and comprising a first surface and a second surface axially spaced apart from each other;
a second part slidably disposed relative to the first part and comprising
  a first proximally-extending resilient arm with an outward protrusion configured to engage the first surface of the first part such that movement of the first part causes movement of the second part,
  a first ramped portion configured to engage the second surface of the first part to cause inward deflection of the first proximally-extending resilient arm when the first ramped portion and the second surface move axially relative to each other, and
  a second portion configured to engage a second resilient arm of the auto-injector such that the second resilient arm outwardly deflects relative to the second part to release a plunger rod of the auto-injector from being held in a distal position within the housing such that the plunger rod moves proximally relative to the housing under a proximally-directed biasing force of a drive spring of the auto-injector to dispense the medicament from the syringe.

17. The auto-injector of claim 16, comprising a syringe carrier disposed within the housing and comprising a proximal portion configured to engage a proximal necked portion of the syringe to limit proximal movement of the syringe relative to the syringe carrier.

18. The auto-injector of claim 17, comprising a sleeve at least partially disposed within the second part and configured to (i) prevent inward deflection of the first proximally-extending resilient arm when the sleeve and the second part are in a first position relative to each other and (ii) allow inward deflection of the first proximally-extending resilient arm when the sleeve and the second part are in a second position relative to each other, the second part and the sleeve configured to move axially relative to each other from the first position to the second position.

19. The auto-injector of claim 16, comprising a third part comprising a third proximally-extending resilient arm configured to releasably engage a surface of the plunger rod to releasably couple proximal movement between the third part and the plunger rod as the plunger rod moves proximally relative to the housing to dispense the medicament from the syringe.

20. The auto-injector of claim 19, wherein the third proximally-extending resilient arm is configured to releasably couple proximal movement between the third part and the plunger rod such that (i) the third part and the plunger rod proximally move together for a first distance as the plunger rod moves proximally relative to the housing to dispense the medicament from the syringe and (ii) the third part is decoupled from the plunger rod for a second distance as the plunger rod moves proximally relative to the housing to dispense the medicament from the syringe.

21. The auto-injector of claim 16, wherein the auto-injector is configured such that distal movement of a proximal end of the auto-injector causes a needle sleeve spring disposed between the second part and the housing to compress, the first part to move relative to the housing, and the second part to move relative to the housing.

22. The auto-injector of claim 21, wherein the proximal end of the auto-injector is configured to contact a body of a user and move distally relative to the housing when pressed against the body of the user.

23. A method comprising:

moving a first part of an auto-injector and a sleeve of the auto-injector axially relative to each other to align an opening of the sleeve with a portion of a first proximally-extending resilient arm of the first part, an outward protrusion of the first proximally-extending resilient arm engaged to a first surface of a second part of the auto-injector such that movement of the second part causes movement of the first part while the first part and the sleeve are moved relative to each other to align the opening of the sleeve with the portion of the first proximally-extending resilient arm;

moving the second part and the first part relative to each other while the opening is aligned with the portion of the first proximally-extending resilient arm such that a ramped portion of the first part engages with a second surface of the second part and the portion of the first proximally-extending resilient arm inwardly deflects into the opening of the sleeve, the first surface and the second surface being axially spaced apart from each other; and moving the first part and the sleeve relative to each other to allow a second resilient arm of the auto-injector to outwardly deflect to release a plunger rod of the auto-injector from being held in a distal position within a housing of the auto-injector causing the plunger rod to proximally move relative to the housing, the sleeve, the first part, and the second part under a proximally-directed biasing force of a drive spring to dispense a medicament from a syringe disposed within the housing, a proximal necked portion of the syringe engaged to a proximal portion of a syringe carrier to limit proximal movement of the syringe relative to the syringe carrier, the housing having at least one viewing window for viewing the syringe.

24. The method of claim 23, comprising engaging an inner surface of the portion of the first proximally-extending resilient arm with an outer surface of the sleeve to prevent inward deflection of the portion of the first proximally-extending resilient arm prior to aligning the opening with the portion of the first proximally-extending resilient arm.

25. The method of claim 23, comprising inwardly deflecting the portion of the first proximally-extending resilient arm from a relaxed position in which the outward protrusion of the first proximally-extending resilient arm is engaged to the first surface of the second part to a deflected position in which the portion of the first proximally-extending resilient arm is received in the opening of the sleeve.

26. The method of claim 23, comprising distally moving a proximal end of the auto-injector relative to the housing to release the plunger rod from being held in the distal position within the housing.

27. The method of claim 26, wherein distally moving the proximal end of the auto-injector relative to the housing causes a needle sleeve spring of the auto-injector to compress, the first part to move relative to the housing, and the second part to move relative to the housing.

28. The method of claim 23, comprising axially coupling an axial end of the sleeve to the syringe.

29. The method of claim 23, comprising coupling an outward protrusion of the sleeve to the housing to limit axial movement of the sleeve relative to the housing.

30. The method of claim 23, comprising engaging a third proximally-extending resilient arm of a third part of the auto-injector to the plunger rod to releasably couple axial movement between the third part and the plunger rod while the plunger rod moves relative to the housing to dispense the medicament from the syringe.

* * * * *